US 11,299,456 B2

(12) United States Patent
Cals et al.

(10) Patent No.: US 11,299,456 B2
(45) Date of Patent: Apr. 12, 2022

(54) ROR GAMMA (RORγ) MODULATORS

(71) Applicants: Lead Pharma Holding B.V., Oss (NL); Sanofi, Paris (FR)

(72) Inventors: Joseph Maria Gerardus Barbara Cals, Oss (NL); David Machnik, Paris (FR); Sander Bernardus Nabuurs, Oss (NL); Jean-Francois Sabuco, Paris (FR)

(73) Assignees: LEAD PHARMA HOLDING B.V., Oss (NL); SANOFI, Paris (FR)

( * ) Notice: Subject to any disclaimer, the term of this patent is extended or adjusted under 35 U.S.C. 154(b) by 0 days.

(21) Appl. No.: 16/710,782

(22) Filed: Dec. 11, 2019

(65) Prior Publication Data
US 2020/0190028 A1  Jun. 18, 2020

Related U.S. Application Data

(63) Continuation of application No. 16/225,894, filed on Dec. 19, 2018, now abandoned, which is a continuation of application No. 15/829,226, filed on Dec. 1, 2017, now Pat. No. 10,196,350.

(30) Foreign Application Priority Data

Dec. 5, 2016  (EP) ..................... 16202175

(51) Int. Cl.
| C07C 317/32 | (2006.01) |
| A61K 31/10 | (2006.01) |
| A61K 31/167 | (2006.01) |
| C07C 317/44 | (2006.01) |
| C07C 317/46 | (2006.01) |
| A61P 17/00 | (2006.01) |
| A61P 19/02 | (2006.01) |
| A61P 1/00 | (2006.01) |
| A61P 25/00 | (2006.01) |
| C07C 315/04 | (2006.01) |

(52) U.S. Cl.
CPC ............ *C07C 317/32* (2013.01); *A61K 31/10* (2013.01); *A61K 31/167* (2013.01); *A61P 1/00* (2018.01); *A61P 17/00* (2018.01); *A61P 19/02* (2018.01); *A61P 25/00* (2018.01); *C07C 315/04* (2013.01); *C07C 317/44* (2013.01); *C07C 317/46* (2013.01); *C07C 2601/02* (2017.05)

(58) Field of Classification Search
CPC .................................................. C07C 317/32
See application file for complete search history.

(56) References Cited

U.S. PATENT DOCUMENTS

| 10,118,895 B2 | 11/2018 | Cals |
| 10,196,350 B2 | 2/2019 | Cals |
| 10,259,782 B2 | 4/2019 | Cals |
| 10,315,996 B2 | 6/2019 | Cals |
| 2007/0154487 A1 | 7/2007 | Littman et al. |
| 2015/0072980 A1 | 3/2015 | Vankayalapati et al. |

(Continued)

FOREIGN PATENT DOCUMENTS

| EP | 3101009 A1 | 12/2016 |
| JP | 2019026575 | 2/2019 |

(Continued)

OTHER PUBLICATIONS

Chaudhary, S.S. et al. (Nov. 22, 2013). "Preparation of Aryl and Heteroaryl Amide Compounds as RORγt Modulator," Accession No. 2013:1808065, Document No. 159:742606 CAPLUS, Glen Mark Pharmaceuticals S.A., two pages.
Golub, T.R. et al. (1999). "Molecular Classification of Cancer: Class Discovery and Class Prediction by Gene Expression Monitoring," Science, 286:531-537.

(Continued)

*Primary Examiner* — Shawquia Jackson
(74) *Attorney, Agent, or Firm* — Morrison & Foerster LLP

(57) ABSTRACT

The present application relates to compounds according to (Formula IA) or (Formula IB):

(Formula IA)

(Formula IB)

or a pharmaceutically acceptable salt thereof.
The compounds can be used as inhibitors of RORγ and are useful for the treatment of RORγ mediated diseases.

6 Claims, No Drawings

(56) References Cited

U.S. PATENT DOCUMENTS

| | | |
|---|---|---|
| 2015/0133437 A1 | 5/2015 | Aicher et al. |
| 2015/0218160 A1 | 8/2015 | Claremon et al. |
| 2015/0291607 A1 | 10/2015 | Bakonyi et al. |
| 2016/0304448 A1 | 10/2016 | Cals |
| 2016/0311830 A1 | 10/2016 | Finsinger et al. |
| 2016/0326163 A1 | 11/2016 | Das et al. |
| 2018/0162809 A1 | 6/2018 | Cals |
| 2018/0162815 A1 | 6/2018 | Cals |
| 2018/0170863 A1 | 6/2018 | Cals |
| 2018/0170877 A1 | 6/2018 | Cals |
| 2018/0215707 A1 | 8/2018 | Sharma et al. |
| 2019/0040012 A1 | 2/2019 | Cals |
| 2019/0119204 A1 | 4/2019 | Cals |

FOREIGN PATENT DOCUMENTS

| | | | | |
|---|---|---|---|---|
| WO | WO-2013171729 A3 * | 2/2014 | ........... | C07D 231/12 |
| WO | WO2015082533 A1 | 6/2015 | | |
| WO | 2015101928 A1 | 7/2015 | | |
| WO | 2016185342 A1 | 11/2016 | | |
| WO | WO2017021879 A1 | 2/2017 | | |
| WO | 2017213137 A1 | 12/2017 | | |

OTHER PUBLICATIONS

Lala. P.K. et al. (1998). "Role of Nitric Oxide in Tumor Progression: Lessons from Experimental Tumors," Cancer and Metastasis Reviews 17(1):91-106.

Medline Plus. Cancer [online], located at URL http://www.nlm.nih.gov/medlineplus/cancer.html, retrieved on Jul. 6, 2007, ten pages.

* cited by examiner

ROR GAMMA (RORγ) MODULATORS

This application is a continuation of U.S. patent application Ser. No. 16/225,894, filed Dec. 19, 2018, which is a continuation of U.S. patent application Ser. No. 15/829,226, filed Dec. 1, 2017, which claims priority benefit of European patent application 16202175.2, filed Dec. 5, 2016, the disclosures of each of which are incorporated herein by reference in their entireties.

The present application relates to compounds that are modulators of RORγ, to pharmaceutical compositions comprising the same and to their use for the treatment of RORγ-mediated diseases or conditions, in particular autoimmune diseases and inflammatory diseases.

T helper ($T_H$) cells play a crucial role in the adaptive immune system as they coordinate defense against specific pathogens. The interleukin 17 (IL-17) producing lineages of $T_H$ cells, such as $T_H17$ cells, have been directly implicated in the pathology of a multitude of autoimmune and inflammatory diseases, including, but not limited to, psoriasis, multiple sclerosis, rheumatoid arthritis, Crohn's disease, asthma, chronic obstructive pulmonary disease, atopic dermatitis, psoriatic arthritis, ankylosing spondylitis and irritable bowel disease.

Interleukin 17 and interleukin 23 (IL-23) are two pivotal cytokines in $T_H17$ biology. IL-17 is secreted by $T_H17$ cells and is a potent inducer of tissue inflammation; IL-23 has been shown to be a key participant in amplifying and stabilizing the proliferation of the $T_H17$ cell type via the IL-23 receptor (IL-23R).

The retinoic-acid-receptor-related orphan receptor γt (RORγt) acts as a master regulator of the development of $T_H17$ cells, and also as a critical component in non-$T_H17$ IL-17 producing cells, such as for example γδ T-cells. The ROR gene family is part of the nuclear hormone receptor superfamily, and consists of three members (RORα, RORβ, and RORγ). Each gene is expressed in different isoforms, differing foremost in their N-terminal sequence. Two isoforms of RORγ have been identified: RORγ1 and RORγ2 (also known as RORγt). The term RORγ is used here to describe both RORγ1 and/or RORγ2.

RORγ modulator compounds have been described in the international patent application WO2015/082533.

Given the important role of RORγ in immune and inflammatory disorders, it is desirable to prepare modulators of RORγ with improved safety profiles which can be used in the treatment of RORγ mediated diseases. The present application provides such novel RORγ modulator compounds with improved safety profiles.

The present application thus provides novel RORγ modulator compounds represented by the (Formula I):

(Formula I)

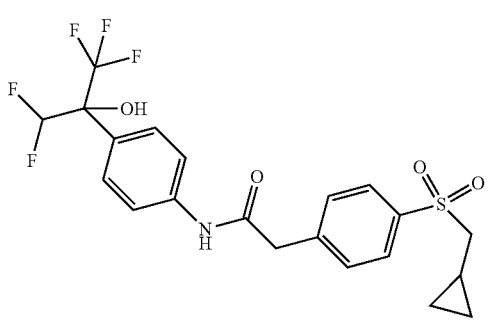

and the absolute configuration of compound (I) corresponds to compounds of (Formula IA) or (Formula IB):

(Formula IA)

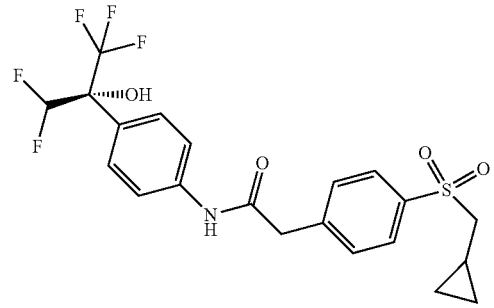

2-{4-[(cyclopropylmethyl)sulfonyl]phenyl}-N-{4-[(1R)-1-(difluoromethyl)-2,2,2-trifluoro-1-hydroxyethyl]phenyl}acetamide or a pharmaceutically acceptable salt thereof.

(Formula IB)

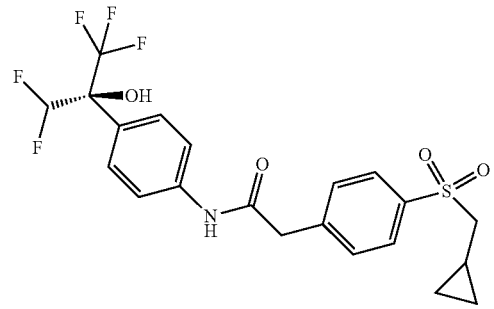

2-{4-[(cyclopropylmethyl)sulfonyl]phenyl}-N-{4-[(1S)-1-(difluoromethyl)-2,2,2-trifluoro-1-hydroxyethyl]phenyl}acetamide or a pharmaceutically acceptable salt thereof.

Unless otherwise indicated, the following definitions are set forth to illustrate and define the meaning and scope of the various terms used to describe the elements of this present application herein.

The term pharmaceutically acceptable salt of the compound represented by the aforementioned (Formula I), (Formula IA) or (Formula IB) represents those salts which are, within the scope of medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. The acid function of the compound can be reacted with an organic or a mineral base, like sodium hydroxide, potassium hydroxide or lithium hydroxide.

In addition to the compound represented by the aforementioned (Formula I), (Formula IA) or (Formula IB), a pharmaceutically acceptable salt thereof, their solvates and hydrates also fall within the scope of the present application.

In another aspect of the present application, it was discovered that the compound of the present application (Formula I), (Formula IA) or (Formula IB) could also be administered as prodrug.

The prodrugs are defined as compounds of (Formula VI), (Formula VIA), (Formula VIB), (Formula VIC) or (Formula VID) where they correspond to compounds of (Formula I), (Formula IA) or (Formula IB) with a sulfinyl group instead of a sulfonyl group. Absolute configuration of chiral centers of prodrugs were not determined and were arbitrarily assigned. It is known by the man skilled in the art that sulfoxides might display improved aqueous solubility when compared to their sulfone counterparts.

(Formula VI)

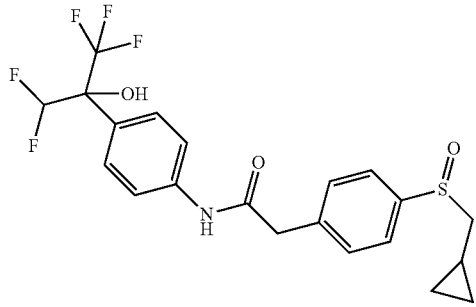

2-[4-(cyclopropylmethylsulfinyl)phenyl]-N-[4-[1-(difluoromethyl)-2,2,2-trifluoro-1-hydroxy-ethyl]phenyl]acetamide.

(−)-2-[4-[(S)-cyclopropylmethylsulfinyl]phenyl]-N-[4-[(1R)-1-(difluoromethyl)-2,2,2-trifluoro-1-hydroxy-ethyl]phenyl]acetamide or a pharmaceutically acceptable salt thereof.

(Formula VIB)

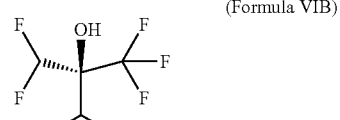

(−)-2-[4-[(S)-cyclopropylmethylsulfinyl]phenyl]-N-[4-[(1S)-1-(difluoromethyl)-2,2,2-trifluoro-1-hydroxy-ethyl]phenyl]acetamide or a pharmaceutically acceptable salt thereof.

(Formula VIA)

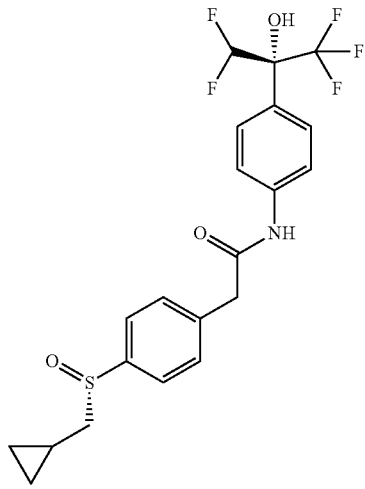

(Formula VIC)

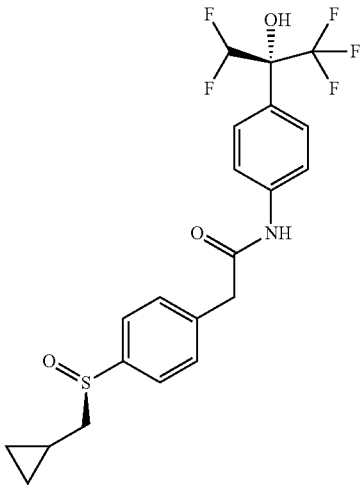

(+)-2-[4-[(R)-cyclopropylmethylsulfinyl]phenyl]-N-[4-[(1R)-1-(difluoromethyl)-2,2,2-trifluoro-1-hydroxy-ethyl]phenyl]acetamide or a pharmaceutically acceptable salt thereof.

(Formula VID)

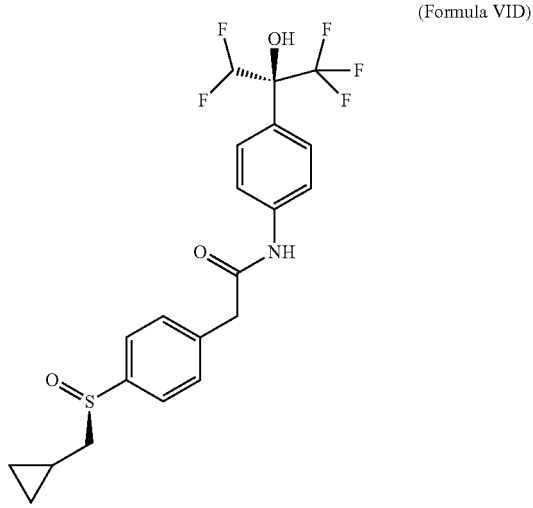 [SMILES: O=C(Cc1ccc([S@](=O)CC2CC2)cc1)Nc1ccc([C@](O)(C(F)F)C(F)(F)F)cc1]

(+)-2-[4-[(R)-cyclopropylmethylsulfinyl]phenyl]-N-[4-[(1S)-1-(difluoromethyl)-2,2,2-trifluoro-1-hydroxy-ethyl]phenyl]acetamide or a pharmaceutically acceptable salt thereof.

Further, the compounds of the present application present no significant toxicities and thus are suitable to be used in a medicament.

The compounds of the application inhibit RORγ activity. Modulation of RORγ activity can be measured using for example biophysical (natural) ligand displacement studies, biochemical AlphaScreen or FRET assays, cellular GAL4 reporter gene assays, cellular IL-17 promotor reporter assay or functional IL-17 ELISA assays using for example mouse splenocytes or human peripheral blood mononuclear cells (PBMCs) cultured under $T_H17$ polarizing conditions.

In such assays, the interaction of a compound with RORγ can be determined by measuring, for example, the compound modulated interaction of cofactor-derived peptides with the RORγ ligand binding domain ($IC_{50}$), or measuring the gene products of compound modulated RORγ mediated transcription using, for example, luciferase reporter assays or IL-17 ELISA assays.

The skilled artisan will recognize that desirable $IC_{50}$ values are dependent on the compound tested. For example, a compound with an $IC_{50}$ value against the biological target less than $10^{-5}$ M is generally considered as a candidate for drug selection. In some embodiments, this value is lower than $10^{-6}$ M.

The safety profile was assessed by human ether-a-go-go-related gene (hERG) ion channel inhibition and CYP3A4 inhibition.

The human ether-a-go-go-related gene (hERG, Kv 11.1) channel plays an especially important role in cardiac safety, and the hERG patch clamp assay is a key regulatory requirement before first-in-man clinical trials (FDA guidance).

Inhibition of the hERG current (IKr), involved in the repolarisation phase of the cardiac action potential, has been shown to prolong the cardiac action potential and to cause QT interval prolongation in electrocardiogram resulting in an increase of the risk for potentially fatal ventricular arrhythmias called "Torsade de Pointes" in humans.

The hERG assay, in which hERG is brought to expression in CHO cells, provides information of the interaction of a compound with the hERG channel. The amplitude of hERG potassium channel tail currents are recorded under control and the compound solution at different concentrations. Then the $IC_{50}$ value is determined from the dose-response curve.

The identification of CYP3A4 inhibition as early as possible in drug discovery is key to prevent potential adverse toxic effects related to drug-drug interactions (FDA guidance).

In the CYP3A4 inhibition assay, in vitro $IC_{50}$ of a test compound as direct inhibitor against is CYP3A4 is determined, by measuring the inhibition of the turn-over of probe substrates of CYP3A4 (Midazolam and Testosterone) to their specific metabolites i.e., 1"-Hydroxymidazolam, 6β-Hydroxytestosterone, in human liver microsomes.

The skilled artisan will recognize that desirable $IC_{50}$ values are dependent on the compound tested. For example, the higher the $IC_{50}$ values are in above tests, the better the safety profile will be, with decreased risks of cardiac safety issues and potential adverse toxic effects related to drug-drug interactions.

The present application also relates to a pharmaceutical composition comprising a compound of (Formula I), (Formula IA) or (Formula IB) or pharmaceutically acceptable salt thereof of compounds in admixture with pharmaceutically acceptable excipients and optionally other therapeutically active agents.

The present application also relates to a pharmaceutical composition comprising a compound of (Formula IA) or (Formula IB) or pharmaceutically acceptable salt thereof of compounds in admixture with pharmaceutically acceptable excipients and optionally other therapeutically active agents.

The present application also relates to a pharmaceutical composition comprising a compound of (Formula I), (Formula IA) or (Formula IB) or pharmaceutically acceptable salt thereof and one or more pharmaceutically acceptable excipients.

The present application also relates to a pharmaceutical composition comprising a compound of (Formula IA) or (Formula IB) or a pharmaceutically acceptable salt thereof and one or more pharmaceutically acceptable excipients.

The excipients must be "acceptable" in the sense of being compatible with the other ingredients of the composition and not deleterious to the recipients thereof.

The present application also relates to a pharmaceutical composition comprising at least one additional therapeutically active agent.

The application further includes a compound of (Formula I), (Formula IA) or (Formula IB) in combination with one or more other drug(s).

The application further includes a compound of (Formula IA) or (Formula IB) in combination with one or more other drug(s).

Compositions include, e.g., those suitable for oral, sublingual, subcutaneous, intravenous, intramuscular, nasal, local, or rectal administration, and the like, all in unit dosage forms for administration.

For oral administration, the compound of the application may be presented as discrete units, such as tablets, capsules, powders, granulates, solutions, suspensions, and the like.

For parenteral administration, the pharmaceutical composition of the compound of the application may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable excipients, the active agent may be compressed into solid dosage units, such as pills, tablets, or be processed into capsules or suppositories. By means of pharmaceutically acceptable liquids, the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable excipients, which do not interfere with the function of the active compounds can be used. Suitable excipients with which the compound of the application can be administered as solid compositions include lactose, starch, cellulose derivatives and the like, or mixtures thereof, used in suitable amounts. For parenteral administration aqueous suspensions, isotonic saline solutions and sterile injectable solutions may be used, containing pharmaceutically acceptable dispersing agents and/or wetting agents, such as propylene glycol or butylene glycol.

The application further includes a pharmaceutical composition, as herein before described, in combination with packaging material suitable for said composition, said packaging material including instructions for the use of the composition for the use as hereinbefore described.

The exact dose and regimen of administration of the compound of the application, or a pharmaceutical composition thereof, may vary with the particular compound, the route of administration, and the age and condition of the individual subject to whom the medicament is to be administered.

In general parenteral administration requires lower dosages than other methods of administration, which are more dependent upon absorption. However, a dosage for humans preferably contains 0.0001-100 mg per kg body weight. The desired dose may be presented as one dose or as multiple sub-doses administered at appropriate intervals throughout the day.

The compounds of (Formula I), (Formula IA) or (Formula IB) according to the application or a pharmaceutically acceptable salt thereof can be used as medicament.

The compounds of (Formula IA) or (Formula IB) according to the application or a pharmaceutically acceptable salt thereof can be used as medicament.

The compounds of (Formula I), (Formula IA) or (Formula IB) according to the application or a pharmaceutically acceptable salt thereof can be used as medicament in therapy.

The compounds of (Formula IA) or (Formula IB) according to the application or a pharmaceutically acceptable salt thereof can be used as medicament in therapy.

A further aspect of the application resides in the use of compounds of (Formula I), (Formula IA) or (Formula IB) according to the application or a pharmaceutically acceptable salt thereof in therapy.

A further aspect of the application resides in the use of compounds of (Formula IA) or (Formula IB) according to the application or a pharmaceutically acceptable salt thereof in therapy.

A further aspect of the application resides in the use of compounds of (Formula I), (Formula IA) or (Formula IB) according to the application or a pharmaceutically acceptable salt thereof for the treatment of RORγ-mediated diseases or RORγ mediated conditions.

A further aspect of the application resides in the use of compounds of (Formula IA) or (Formula IB) according to the application or a pharmaceutically acceptable salt thereof for the treatment of RORγ-mediated diseases or RORγ mediated conditions.

Another aspect of the application resides in the use of compounds of (Formula I), (Formula IA) or (Formula IB) according to the application or a pharmaceutically acceptable salt thereof for the treatment of autoimmune diseases, in particular those diseases in which $T_H17$ cells and non-$T_H17$ cells, which express $T_H17$ hallmark cytokines, play a prominent role.

Another aspect of the application resides in the use of compounds of (Formula IA) or (Formula IB) according to the application or a pharmaceutically acceptable salt thereof for the treatment of autoimmune diseases, in particular those diseases in which $T_H17$ cells and non-$T_H17$ cells, which express $T_H17$ hallmark cytokines, play a prominent role.

These include, but are not limited to, the treatment of rheumatoid arthritis, psoriasis, inflammatory bowel disease, Crohn's disease and multiple sclerosis.

In another aspect, compounds of (Formula I), (Formula IA) or (Formula IB) according to the application or a pharmaceutically acceptable salt thereof can be used for treatment of inflammatory diseases in which $T_H17$ cells and/or non-$T_H17$ cells, which express $T_H17$ hallmark cytokines, play a prominent role such as, but not limited to respiratory diseases, osteoarthritis and asthma.

In another aspect, compounds of (Formula IA) or (Formula IB) according to the application or a pharmaceutically acceptable salt thereof can be used for treatment of inflammatory diseases in which $T_H17$ cells and/or non-$T_H17$ cells, which express $T_H17$ hallmark cytokines, play a prominent role such as, but not limited to respiratory diseases, osteoarthritis and asthma.

Also, compounds of (Formula I), (Formula IA) or (Formula IB) or a pharmaceutically acceptable salt thereof can be used for treatment of infectious diseases in which $T_H17$ cells and/or non-TH17 cells, which express $T_H17$ hallmark cytokines, play a prominent role such as, but not limited to mucosal leishmaniasis.

Also, compounds of (Formula IA) or (Formula IB) or a pharmaceutically acceptable salt thereof can be used for treatment of infectious diseases in which $T_H17$ cells and/or non-$T_H17$ cells, which express $T_H17$ hallmark cytokines, play a prominent role such as, but not limited to mucosal leishmaniasis.

Compounds of (Formula I), (Formula IA) or (Formula IB) according to the application or a pharmaceutically acceptable salt thereof can also be used for treatment of other diseases in which $T_H17$ cells and/or non-$T_H17$ cells, which express $T_H17$ hallmark cytokines, play a prominent role such as, but not limited to Kawaski disease and Hashimoto's thyroiditis.

Compounds of (Formula IA) or (Formula IB) according to the application or a pharmaceutically acceptable salt thereof can also be used for treatment of other diseases in which $T_H17$ cells and/or non-$T_H17$ cells, which express $T_H17$ hallmark cytokines, play a prominent role such as, but not limited to Kawaski disease and Hashimoto's thyroiditis.

In yet another aspect, the application resides in the use of compounds of (Formula I), (Formula IA) or (Formula IB) according to the application or a pharmaceutically acceptable salt thereof for the treatment of multiple sclerosis, inflammatory bowel disease, Crohn's disease, psoriasis, rheumatoid arthritis, asthma, osteoarthritis, Kawaski disease, Hashimoto's thyroiditis, cancer and mucosal leishmaniasis.

In yet another aspect, the application resides in the use of compounds of (Formula IA) or (Formula IB) according to the application or a pharmaceutically acceptable salt thereof for the treatment of multiple sclerosis, inflammatory bowel disease, Crohn's disease, psoriasis, rheumatoid arthritis, asthma, osteoarthritis, Kawaski disease, Hashimoto's thyroiditis, cancer and mucosal leishmaniasis.

In another aspect, the compounds of (Formula I), (Formula IA) or (Formula IB) according to the application or a pharmaceutically acceptable salt thereof for the preparation of a medicament can be used in therapies to treat or prevent multiple sclerosis, inflammatory bowel disease, Crohn's disease, psoriasis and rheumatoid arthritis, asthma, osteoarthritis, Kawaski disease, Hashimoto's thyroiditis, cancer and mucosal leishmaniasis.

In another aspect, the compounds of (Formula IA) or (Formula IB) according to the application or a pharmaceutically acceptable salt thereof for the preparation of a medicament can be used in therapies to treat or prevent multiple sclerosis, inflammatory bowel disease, Crohn's disease, psoriasis and rheumatoid arthritis, asthma, osteoarthritis, Kawaski disease, Hashimoto's thyroiditis, cancer and mucosal leishmaniasis.

In another aspect, the compounds of (Formula I), (Formula IA) or (Formula IB) according to the application or a pharmaceutically acceptable salt thereof can be used to treat or prevent psoriasis.

In another aspect, the compounds of (Formula IA) or (Formula IB) according to the application or a pharmaceutically acceptable salt thereof can be used to treat or prevent psoriasis.

In yet another aspect, the compounds of (Formula I), (Formula IA) or (Formula IB) according to the application or a pharmaceutically acceptable salt thereof can be used to treat inflammatory bowel disease.

In yet another aspect, the compounds of (Formula IA) or (Formula IB) according to the application or a pharmaceutically acceptable salt thereof can be used to treat inflammatory bowel disease.

Herein is also provided a method of treating multiple sclerosis, inflammatory bowel disease, Crohn's disease, psoriasis and rheumatoid arthritis, asthma, osteoarthritis, Kawaski disease, Hashimoto's thyroiditis, cancer and mucosal leishmaniasis comprising administering to a patient in need thereof a therapeutically effective amount of (Formula I), (Formula IA) or (Formula IB) or a pharmaceutically acceptable salt thereof.

Herein is also provided a method of treating multiple sclerosis, inflammatory bowel disease, Crohn's disease, psoriasis and rheumatoid arthritis, asthma, osteoarthritis, Kawaski disease, Hashimoto's thyroiditis, cancer and mucosal leishmaniasis comprising administering to a patient in need thereof a therapeutically effective amount of compounds of (Formula VI), (Formula VIA), (Formula VIB), (Formula VIC) or (Formula VID) or a pharmaceutically acceptable salt thereof.

The phrase "therapeutically effective amount," as used herein, means the amount of the subject compound or composition that is effective in producing the desired therapeutic effect.

EXAMPLES

The present application will be explained with reference to examples. However, the scope of the present application is not limited to the following examples.

The compounds of the application can be readily prepared according to the following reaction scheme, or modifications thereof, using readily available starting materials, reagents or previously described intermediates and conventional synthesis procedures.

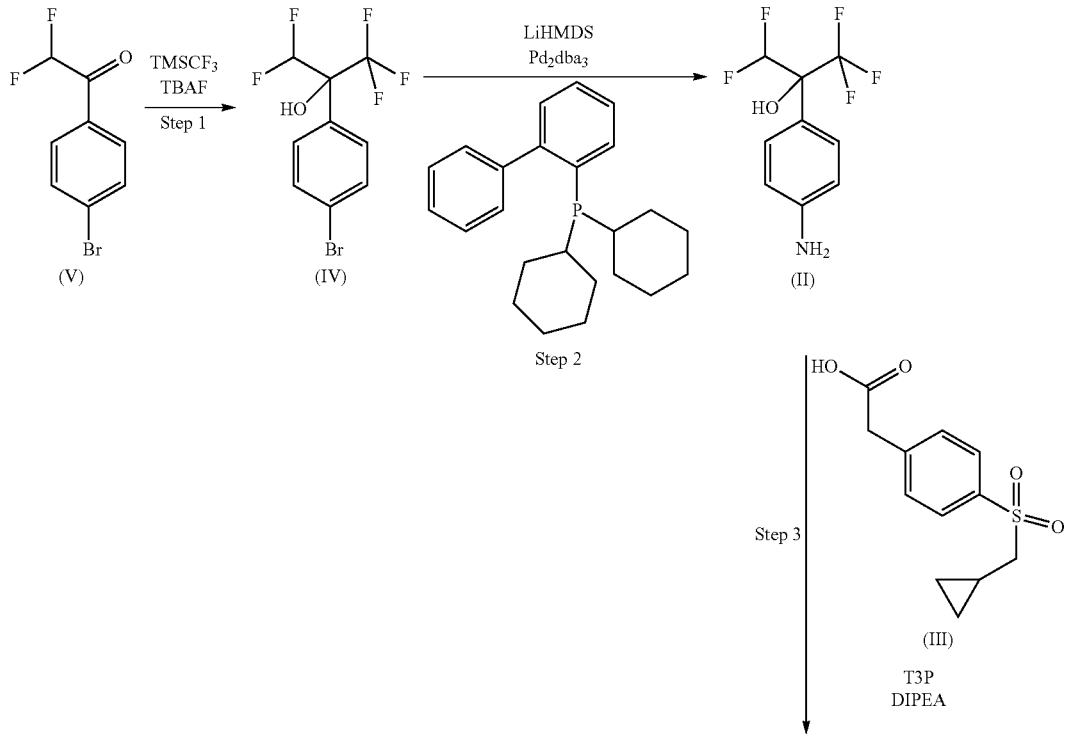

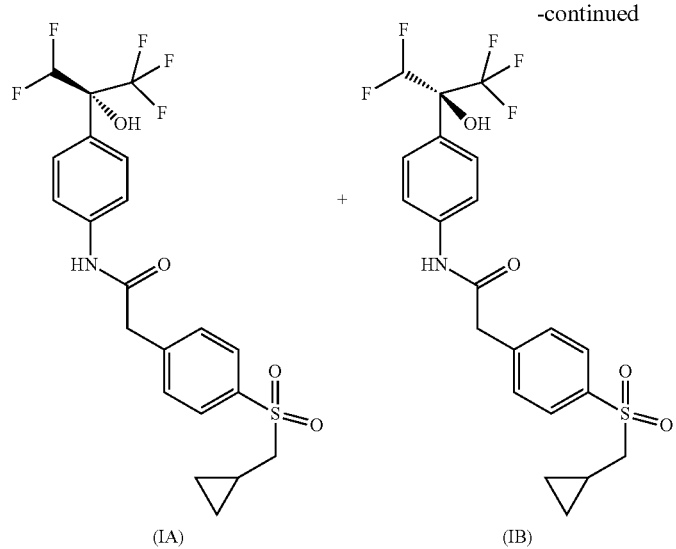

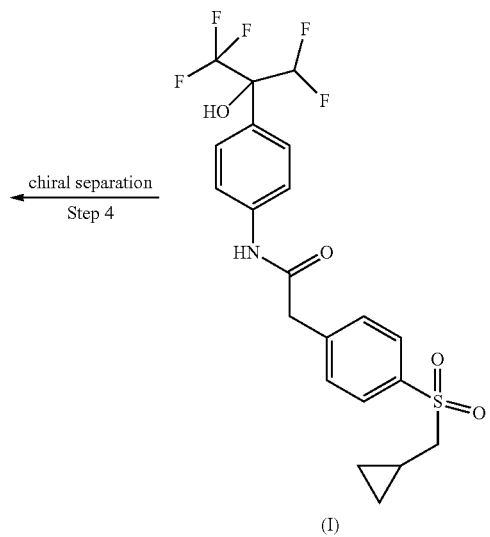

The abbreviations used in this scheme and these experimental details are listed below and additional ones should be considered known to a person skilled in the art of synthetic chemistry.

Abbreviations used herein are as follow: TMSCF$_3$: Trifluoromethyltrimethylsilane; TBAF: Tetra-N-butylammonium fluoride; TMS: Trimethylsilyl; LiHMDS: Lithium bis(trimethylsilyl)amide; Pd$_2$(dba)$_3$: Tris(dibenzylideneacetone)dipalladium(0); T3P: 1-Propanephosphonic anhydride; DIPEA: Diisopropylethylamine, N-ethyl-N-isopropyl-propan-2-amine; RT: room temperature; DMF: Dimethylformamide; CH$_2$Cl$_2$, DCM: dichloromethane; THF: Tetrahydrofuran; Et$_2$O: Diethyl ether; DMSO: Dimethylsulfoxide; EtOH: Ethanol; TLC: Thin Layer Chromatography; EtOAc: ethyl acetate; ACN, CH$_3$CN: acetonitrile; MeOH: methanol; TFA: Trifluoroacetic acid; HCl: Hydrochloric acid; Et$_3$N, TEA: triethylamine; NaCl: sodium chloride; NaHCO$_3$: sodium bicarbonate; H$_2$O: water; MgSO$_4$: magnesium sulfate; Na$_2$SO$_4$: sodium sulfate.

Chemical names are preferred IUPAC names, generated using Accelrys Draw 4.1.

If a chemical compound is referred to using both a chemical structure and a chemical name, and an ambiguity exists between the structure and the name, the structure predominates.

Example 1

2-[4-(cyclopropylmethylsulfonyl)phenyl]-N-[4-[1-(difluoromethyl)-2,2,2-trifluoro-1-hydroxy-ethyl]phenyl]acetamide.

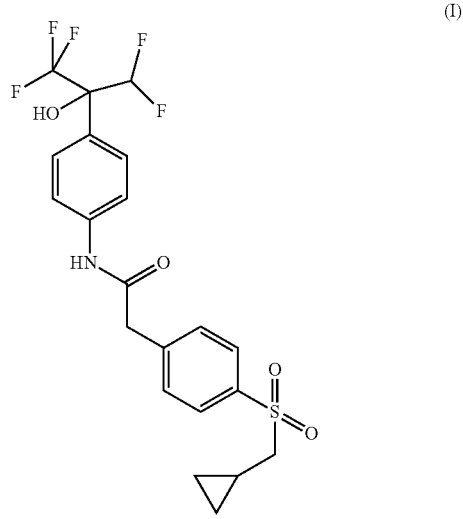 [SMILES: O=C(Cc1ccc(S(=O)(=O)CC2CC2)cc1)Nc1ccc(C(O)(C(F)F)C(F)(F)F)cc1]

Step 1:

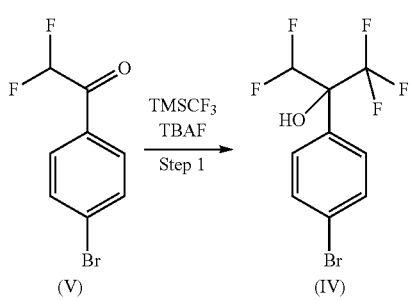

To a solution of 1-(4-bromophenyl)-2,2-difluoro-ethanone (10.5 g) in 100 mL THF at 0° C. under argon was added TMSCF₃ (12.7 g) followed by addition of a 1 M solution of TBAF in THF (90 mL) over 45 minutes. The reaction mixture was stirred for 1 hour at RT, then diluted with Et₂O (200 mL), washed with water (2×200 mL), brine (100 mL), dried and concentrated under reduced pressure. The residue was purified by column chromatography on silica gel, using 0% to 20% EtOAc in cyclohexane as the eluent to give 11.5 g (84%) of 2-(4-bromophenyl)-1,1,1,3,3-pentafluoro-propan-2-ol as a yellow oil.

MS(ES⁺) m/z 302.9/304.9 [M+H]⁺.

¹H NMR (400 MHz, DMSO-d6) δ ppm 6.70 (t, J=53.1 Hz, 2 H), 7.60 (d, J=9.2 Hz, 2 H), 7.69 (d, J=9.2 Hz, 2 H), 7.92 (s, 1 H).

Step 2:

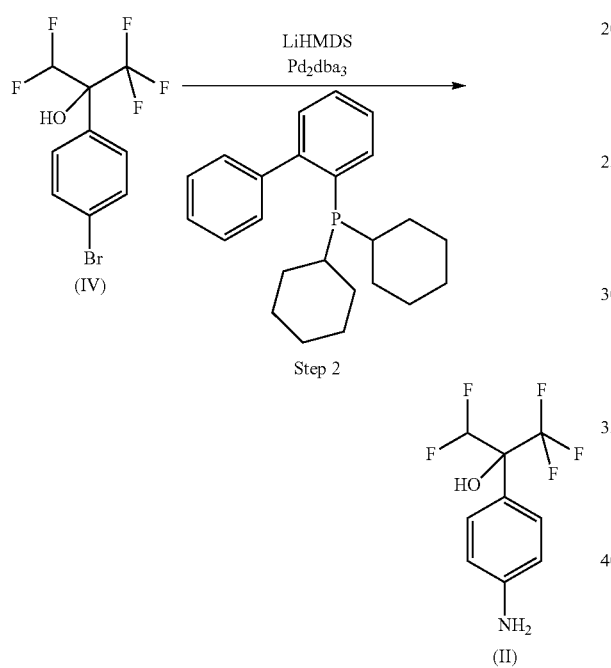

Step 2

To a solution of 2-(4-bromophenyl)-1,1,1,3,3-pentafluoro-propan-2-ol (11.4 g) in THF (100 mL) under argon was added a 1 M solution of LiHMDS in THF (112 mL), 2-(dicyclohexylphosphino)biphenyl (1.6g) followed by addition of Pd₂(dba)₃ (2.16g). The reaction mixture was stirred under reflux for 1 hour, then cooled to 0° C., and a 12N aqueous solution of HCl (15 mL) was added dropwise. After stirring for 1 hour at RT, the reaction mixture was poured onto a saturated aqueous solution of NaHCO₃ (400 mL) then extracted with EtOAc (2×300 mL). The combined organic layers were dried and concentrated under reduced pressure. The product was precipitated in DCM, filtered and washed with a minimal amount of DCM to give the desired product (4.75 g). The filtrate was purified by column chromatography on silica gel, using 0% to 50% EtOAc in cyclohexane as the eluent to give 1.4 g of the desired product. 2-(4-Aminophenyl)-1,1,1,3,3-pentafluoro-propan-2-ol (6.15 g, 68%) was obtained as an off-white solid.

MS(ES⁺) m/z 242.0 [M+H]⁺.

¹H NMR (400 MHz, DMSO-d6) δ ppm 5.27 (s, 2 H), 6.22-6.74 (m, 3 H), 7.11-7.35 (m, 3 H).

Step 3:

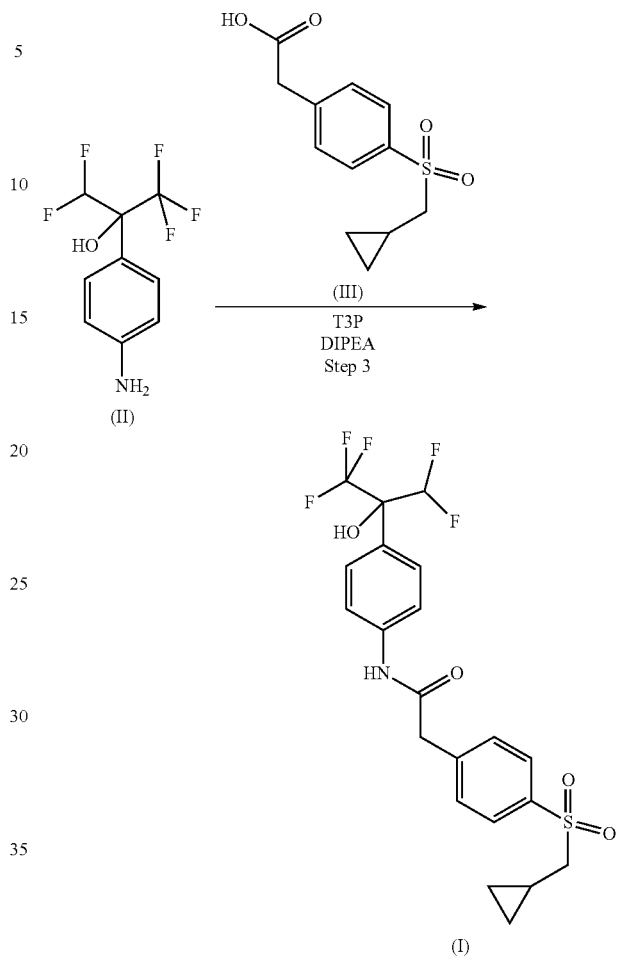

To a solution of 2-(4-aminophenyl)-1,1,1,3,3,3-hexafluoro-propan-2-ol (0.55 g) in DCM (10 mL) were added 2-[4-(cyclopropylmethylsulfonyl)phenyl]acetic acid (0.58 g) and N-ethyl-N-isopropyl-propan-2-amine (1.19 mL) followed by dropwise addition of a 50% solution of T3P in DCM (0.8 mL). The reaction mixture was stirred at RT for 2 hours. EtOAc (100 mL) and water (100 mL) were added. The organic layer was separated, washed with brine (100 mL), dried over MgSO₄, filtered and concentrated under reduced pressure. The residue was triturated in DCM (5 mL), filtered and washed with 10% DCM in pentane (5 mL) then dried to give 0.72 g (66%) of 2-[4-(cyclopropylmethylsulfonyl)phenyl]-N-[4-[1-(difluoromethyl)-2,2,2-trifluoro-1-hydroxy-ethyl]phenyl]acetamide as an off-white solid.

MS(ES⁺) m/z 478.1 [M+H]⁺.

Examples 2 and 3

The two enantiomers were separated from Example 1 by chiral chromatography using a column Chiralpak AD 20 μm, 76.5×350 mm and a mobile phase, EtOH:MeOH 90:10, 350 mL/min, with UV detection at 254 nm.

Starting from 5 g of racemate in 500 mL of EtOH, five injections of the solution were done to yield, after concentration, 2.17 g of Example 2 (first enantiomer to be eluted) and 2.02 g of Example 3.

Example 2—Compound of (Formula IA): (+)-2-[4-(cyclopropylmethylsulfonyl)phenyl]-N-[4-[(1R)-1-(difluoromethyl)-2,2,2-trifluoro-1-hydroxy-ethyl]phenyl]acetamide

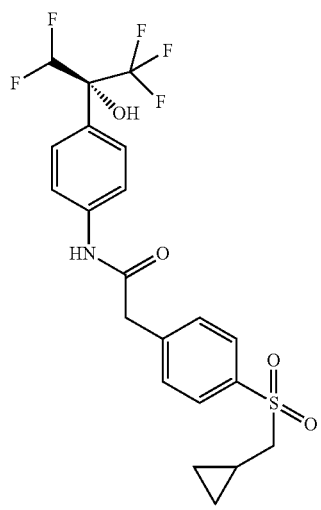

(IA)

MS(ES+) m/z 478.1 [M+H]+.

1H NMR (400 MHz, DMSO-d6) δ ppm 0.11 (m, 2 H), 0.44 (m, 2 H), 0.82 (m, 1 H), 3.24 (d, J=7.2 Hz, 2 H), 3.82 (s, 3 H), 6.67 (t, J=53.4 Hz, 2 H), 7.57 (d, J=9.2 Hz, 2 H), 7.60 (d, J=8.5 Hz, 2 H), 7.67 (d, J=9.2 Hz, 2 H), 7.70 (s, 1 H), 7.86 (d, J=8.5 Hz, 2 H), 10.42 (s, 1 H).

Optical rotation: $[\alpha]_D^{20}$=+1.5° (c=3 mg/mL, DMSO).

Example 3—Compound of (Formula IB): (−)-2-[4-(cyclopropylmethylsulfonyl)phenyl]-N-[4-[(1S)-1-(difluoromethyl)-2,2,2-trifluoro-1-hydroxy-ethyl]phenyl]acetamide

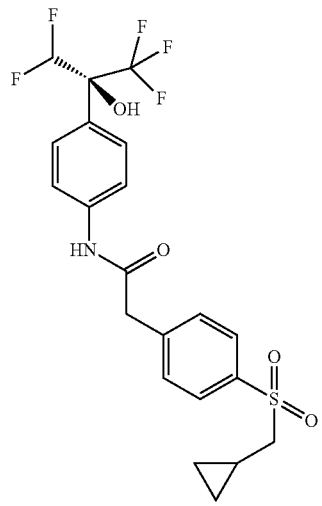

(IB)

MS(ES+) m/z 478.0 [M+H]+.

1H NMR (400 MHz, DMSO-d6) δ ppm 0.11 (m, 2 H), 0.44 (m, 2 H), 0.82 (m, 1 H), 3.24 (d, J=7.2 Hz, 2 H), 3.82 (s, 3 H), 6.67 (t, J=53.4 Hz, 2 H), 7.56 (d, J=9.2 Hz, 2 H), 7.59 (d, J=8.5 Hz, 2 H), 7.67 (d, J=9.2 Hz, 2 H), 7.70 (s, 1 H), 7.86 (d, J=8.5 Hz, 2 H), 10.42 (s, 1 H).

Optical rotation: $[\alpha]_D^{20}$=−4.6° (c=3 mg/mL, DMSO).

Example 4—X-Ray Single Crystal Diffraction

The absolute configuration of Examples 2 and 3 has been determined from X-ray Single Crystal Diffraction (XRSCD) data using anomalous dispersion and Bijvoet differences analysis. A single crystal of suitable crystallographic quality for crystal structure determination from single crystal diffraction data has been isolated from a slow evaporation experiment of a solution of Examples 2 and 3 in chloroform.

Absolute Configuration of Example 2

Data have been collected on a Bruker Smart Apex single crystal diffractometer. A molybdenum IμS microfocus X-ray source has been used, running at 50 kV and 0.6 mA, emitting Mo-Kα radiation (λ=0.710731 Å). A Charge-Coupled Device (CCD chip: 4K, 62 mm) area detector has been positioned at 6.0 cm. An Oxford Cryosystems nitrogen cryostat (Cryostream Plus 700 series) has allowed XRSCD experiment to be carried out at 100 K. The single crystal with a size of: 25×250×250 μm³ has been mounted from a Paratone N™ oil drop onto a low background mylar MiTeGen loop. A full Ewald sphere of reflections has been collected (3 omega scans of 680 frames with a frame width of 0.3°). Accumulation time has been set at 80 seconds for each frame to be acquired.

The orientation matrix and unit cell have been established using CELL_NOW (v2008/4) program. The 3D reflection profile and the integration of all reflections have been carried out with the SAINT (v8.34A) program. The TWINABS (v2012/1) program has been used to correct for Lorentz and polarization effects and for absorption by the sample. In addition, both HKLF4 and HKLF5 data has been generated respectively for solving and refining by the SHELXTL (v2014/7) program suite.

The crystal structure data are as follows:

Triclinic, space group P1
a=7.9892(13) Å, b=11.4301(18) Å, c=11.6936(19) Å
α=83.022(2)°, β=77.006(2)°, γ=81.071(2)°
V=1023.7(3) Å³, Z=2, T=100(2) K,
11704 reflections measured (3.6≤2Θ≤58.2), 11704 unique ($R_{sigma}$=0.0229)
736 parameters and 3 restraints The final $R_1$ is 2.7% (I>2σ(I)) and $wR_2$ is 7.1% (all data) with Gof=1.030.

The standard procedure for the determination of the absolute structure with X-ray diffraction techniques is based on the determination of the Flack parameter (x) with its associated standard uncertainty as part of the least-squares refinement procedure. Expected values are 0 (within 3 esd's) for correct and +1 for inverted absolute structure. In case of Example 2—compound of (Formula IA), Flack x=0.095(33) by classical fit to all intensities and 0.072(21) from 3969 selected quotients (Parsons' method giving a higher precision) indicate that Example 2—compound of (Formula IA) absolute configuration has been reliably determined.

In addition a post-refinement procedure based on a Bayesian statistics approach was applied (a completely different way from Flack approach). Using a combination of maximum likelihood estimation and Bayesian statistics it not only gets a qualitative assignment of the absolute structure, but also a quantitative estimate of the reliability of that assignment. Analysis of Example 2—compound of (Formula IA) absolute structure using likelihood method has been performed using Olex2 software package. The resulting value is Hooft y=0.13(5) indicating that the absolute structure has been determined correctly (Bijvœt pair analysis using Student's t distribution with 88% Bijvœt pairs coverage: 4639 pairs used). The method has also calculated that the probability that the structure is inverted is equal to zero.

Thus, these results indicate that the absolute configuration of Example 2—compound of (Formula IA) is R (probability of 100%).

Absolute Configuration of Example 3

Data have been collected on a Bruker Smart Apex single crystal diffractometer. A molybdenum IµS microfocus X-ray source has been used, running at 50 kV and 0.6 mA, emitting Mo-Kα radiation (λ=0.710731 Å). A Charge-Coupled Device (CCD chip: 4K, 62 mm) area detector has been positioned at 6.0 cm. An Oxford Cryosystems nitrogen cryostat (Cryostream Plus 700 series) has allowed XRSCD experiment to be carried out at 100 K. The single crystal with a size of: 40×150×200 µm$^3$ has been mounted from a Paratone N™ oil drop onto a low background mylar MiTeGen loop. A full Ewald sphere of reflections has been collected (3 omega scans of 680 frames with a frame width of 0.3°). Accumulation time has been set at 75 seconds for each frame to be acquired.

The orientation matrix and unit cell has been established using the Bruker AXS Apex2 (v2014.11 0) program suite. The 3D reflection profile and the integration of all reflections have been carried out with the SAINT (v8.34A) program. The SADABS (v2014/5) program has been used to correct for Lorentz and polarization effects and for absorption by the sample. The tentative space group has been determined with the XPREP (v2014/2) program. The SHELXTL XT (v2014/4) program has been used to solve the structure by the intrinsic phasing method. The SHELXTL XLMP (v2014/7) program has been used to refine the solution by full-matrix least-squares calculations on $F^2$.

The crystal structure data are as follows:
Triclinic, space group P1
a=8.0022(5) Å, b=11.4394(8) Å, c=11.7044(8) Å
α=83.0030(10)°, β=76.9840(10)°, γ=80.9850(10)°
V=1026.83(12) Å$^3$, Z=2, T=100(2) K
10430 reflections measured (3.6≤2Θ≤57.8), 8932 unique ($R_{int}$=0.0081)
737 parameters and 3 restraints
The final $R_1$ was 2.5% (I>2σ(I)) and w$R_2$ was 6.8% (all data) with Gof=1.024.

The standard procedure for the determination of the absolute structure with X-ray diffraction techniques is based on the determination of the Flack parameter (x) with its associated standard uncertainty as part of the least-squares refinement procedure. Expected values are 0 (within 3 esd's) for correct and +1 for inverted absolute structure. In case of Example 3—compound of (Formula IB), Flack x=0.063(47) by classical fit to all intensities and 0.058(9) from 3969 selected quotients (Parsons' method giving a higher precision) indicate that Example 3—compound of (Formula IB) absolute configuration has been reliably determined.

In addition a post-refinement procedure based on a Bayesian statistics approach was applied. Using a combination of maximum likelihood estimation and Bayesian statistics it not only gets a qualitative assignment of the absolute structure, but also a quantitative estimate of the reliability of that assignment.

Analysis of Example 3—compound of (Formula IB) absolute structure using likelihood method has been performed using Olex2 software package. The resulting value is Hooft y=0.059(8) indicating that the absolute structure has been determined correctly (Bijvœt pair analysis using Student's t distribution with 75% Bijvœt pairs coverage: 4049 pairs used). The method has also calculated that the probability that the structure is inverted is equal to zero.

Thus these results indicate that the absolute configuration of Example 3—compound of (Formula IB) is S (probability of 100%).

Example 5—RORγ GAL4 Reporter Gene Assay

Examples 2-3 of the present compound of Formula IA and Compound of Formula IB application and example No. 37 from WO2015/082533 were tested for their ability to inhibit RORγ activity in a RORγ GAL4 reporter gene assay.

The assay procedure is described below and results are presented in Table 1.

A GAL4 one-hybrid reporter system employing luciferase readout was established to determine inhibition of RORγ in 293FT cells. The RORγ ligand-binding domain (LBD) was fused to the yeast GAL4 DNA binding domain (DBD) and placed under the control of the human cytomegalovirus (CMV) immediate early promoter, using expression vector pFN26A (Promega) and standard recombinant DNA cloning methods. To serve as a control in the assay, a similar vector was generated in which the GAL4-DBD was fused to Herpes simplex virus protein 16 (VP16), a constitutive transcriptional activator.

To monitor the inhibitory effect of compounds on RORγ, a transcriptional reporter construct was used. The pGL4.35 vector (Promega) contains nine copies of the GAL4 Upstream Activator Sequence (UAS). This sequence drives the transcription of the luciferase reporter gene luc2P in response to binding of a fusion protein containing the GAL4 DNA binding domain, as for example expressed by the GAL4-RORγ-LBD and GAL4-VP16 expression vectors described above. To allow a GAL4 fusion protein to drive the expression of the luciferase reporter, the pGL4.35 expression vector and the appropriate GAL4 fusion protein expression vector were bulk transfected in the 293FT cells using standard transfection techniques.

The day after transfection, cells were plated into 96 well plates, test compound was added and the plates were incubated overnight. Subsequently, the firefly luciferase activity was quantified using luciferase detection reagent and luminescence readout.

Detailed Assay Description

293FT cells (Invitrogen) were transfected with a GAL4 fusion protein expression vector (as described above) and the transcriptional reporter construct (pGL4.35, Promega). 60 µL of TransIT-293 transfection reagent (Mirus Bio) was added drop wise to 1500 µl Opti-MEM I Reduced Serum Medium (Invitrogen) and incubated at room temperature (RT) for 5 to 20 minutes. 1500 µL of this reagent mixture was added to 5 µg of GAL4 fusion protein expression vector and 5 µg of the transcriptional reporter construct, and incubated at RT for 20 minutes.

To harvest 293FT cells from a T75 flask, first the culture medium was taken off the cells. Subsequently, the cells were washed with Phosphate Buffered Saline (PBS) (Lonza), after which the PBS was removed. To dissociate the cells, 1 ml of TrypLE Express (Invitrogen) was added to the flask, followed by incubation at RT until the cells visually started to detach. Cells were collected in 5 mL of assay medium (DMEM culture medium (Lonza), 10% dialyzed FBS (Invitrogen) and Pen/Strep (Lonza)) to achieve a single cell suspension. 10×10$^6$ cells were spun down and re-suspended in 10 mL of assay medium. Subsequently, the cell suspension was added to the transfection mix tube, and then transferred as a whole to a T75 flask (Greiner), followed by overnight (16-24 hours) incubation at 37° C. and 5% $CO_2$.

For compound screening, the cells were harvested (as described above) and counted. $13 \times 10^6$ cells were spun down, the supernatant was aspirated and the cells were re-suspended in 17.3 mL of assay medium to obtain a cell suspension of $0.75 \times 10^6$ cells/mL. 80 µL of cell suspension (60,000 cells) was plated per well into a white, flat bottom, tissue culture treated, 96 well screening plates (Greiner).

Test compounds were diluted, starting from a 10 mM dimethylsulfoxide (DMSO) stock solution, to serial dilutions in DMSO at 500× the final test concentration. Subsequently, these solutions were diluted to 5× the final test concentration in two 10-fold-dilution steps in assay medium. The final DMSO concentration of the 5× test compound solution was 1%. 20 µL of the 5× test compound solution was added to each test well of the 96 well plate previously plated with 80 µl cell suspension, resulting in the final test concentration with 0.2% DMSO.

The plates were incubated overnight (16-24 hours) at 37° C. and 5% $CO_2$.

For the luciferase readout, the luciferase reagent (Britelite Plus, Perkin Elmer) was brought to RT. To each test well of the screening plates, 100 µL of 2.5-fold diluted Britelite Plus reagent was added, followed by incubation at RT for 10 minutes. The luciferase luminescence signal was measured using a Wallac Victor Microplate Reader (Perkin Elmer).

The half maximum inhibitory concentration ($IC_{50}$) values for the test compounds were calculated from the luciferase signal using GraphPad Prism software (GraphPad Software).

Peripheral blood mononuclear cells were separated from buffy coats (Sanquin) using Ficoll-Paque PREMIUM separation medium (GE Healthcare Life Sciences) according to manufacturer's protocol and re-suspended in assay medium at 37° C.

Test compounds were diluted, starting from a 10 mM dimethylsulfoxide (DMSO) stock solution, to serial dilutions in DMSO at 200× the final test concentration. Subsequently, these solutions were diluted in two dilution steps in assay medium to 5× the final test concentration. The DMSO concentration of the 5× test compound solution was 2.5%.

Anti-CD28 antibody (BD Pharmingen) was diluted to 10 µg/mL in assay medium. The PBMCs were diluted to a concentration of $2.2 \times 10^6$ cells/mL in assay medium at 37° C.

For compound screening, the anti-CD3 coated plates were washed two times with PBS; the wells were subsequently aspirated using vacuum. To each screening well 90 µL of the PBMC suspension, 30 µL of the anti-CD28 solution and 30 µL of the 5× test compound solution was added, resulting in the final test concentration with 0.5% DMSO. All outer wells were filled with PBS to prevent evaporation. Plates were incubated for 5 days at 37° C. and 5% $CO_2$.

After incubation, the plates were spun down at 1500 rpm for 4 minutes and the supernatant was collected. Subsequently, the IL-17A levels in the supernatants was determined using an IL-17A AlphaLISA kit (Perkin Elmer) according to the manufacturer's protocol.

The half maximum inhibitory concentration ($IC_{50}$) values for the test compounds were calculated from the IL-17A signal using GraphPad Prism software (GraphPad Software).

TABLE 1

| Example No | RORγ GAL4 reporter gene assay $pIC_{50}$ | | | PBMC IL-17 assay $pIC_{50}$ | | |
|---|---|---|---|---|---|---|
| | Average | Standard deviation | Number of experiments | Average | Standard deviation | Number of human donors |
| 37 | 7.9 | 0.2 | 5 | 7.9 | 0.2 | 11 |
| 2 | 7.4 | 0.2 | 5 | 7.2 | 0.2 | 11 |
| 3 | 7.9 | 0.2 | 5 | 7.6 | 0.3 | 11 |

Example 6—Peripheral Blood Mononuclear Cell (PBMC) IL-17 Assay

Examples 2-3 of the present application and example No. 37 from WO2015/082533 were tested for their ability to inhibit the IL-17A production in anti-CD3/anti-CD28 stimulated peripheral blood mononuclear cells (PBMCs) isolated from human blood. The assay procedure is described below and results are presented in Table 1.

This assay is designed to measure the levels of IL-17A secreted from anti-CD3/anti-CD28 stimulated PBMCs with the aim of measuring the inhibition of RORγ mediated IL-17A production.

Detailed Assay Description

The assay medium consists of 90% RPMI 1640 (Lonza), 10% heat-inactivated fetal bovin serum (FBS, Lonza) and 100 U/mL penicillin/streptomycin solution.

Anti-CD3 antibody (BD Pharmingen) was diluted to 10 µg/ml in PBS (Lonza). 30 µL of 10 µg/ml anti-CD3 solution was added to the inner 60 wells of a 96-well cell culture treated U-bottom plate (Greiner). Plates were incubated overnight (16-24 hours) at 37° C. and 5% $CO_2$.

Example 7—hERG Channel Protocol

Examples 2-3 of the present application and example No. 37 of WO2015/082533 were tested in vitro against the hERG (human Ether-à-go-go-Related Gene) potassium channel. The assay procedure is described below and results are presented in Table 2.

Detailed Assay Description

Frozen CHO (Chinese hamster ovary) cells stably expressing hERG channels were thawed and seeded on glass coverslips in petri dishes. Cells were cultured in HAM's F-12 media supplemented with 10% fetal bovine serum, 100 IU/mL penicillin, 100 µg/mL streptomycin and 500 µg/mL G418 (Invitrogen, Carlsbad, Calif.) in an atmosphere of 95% air/5% $CO_2$ at 37° C. CHO cells were ready for patch-clamping after culture for 1-5 days. hERG currents were recorded at room temperature using the whole-cell patch-clamp technique with an Axopatch 200B amplifier (Molecular Devices, Sunnyvale Calif.). Electrodes (1-3 MΩ resistance) were fashioned from TW150F glass capillary tubes (World Precision Instruments, Sarasota, Fla.) and filled with a solution containing (in mM): potassium aspartate 120; KCl 20; Na₂ATP 4; HEPES 5; MgCl₂ 1; pH 7.2 adjusted with KOH. The external recording solution contained (in mM): NaCl 130; KCl 4; sodium acetate 2.8; MgCl₂ 1; HEPES, 10; glucose 10; CaCl₂ 1 at pH 7.4 adjusted with NaOH. hERG currents were elicited by 2 s depolarizing pulses to +20 mV followed by repolarization to −40 mV for 1.6 s from a −80 mV holding potential at a frequency of 0.1 Hz. Currents were analyzed using the pCLAMP suite of software (Molecular Devices). IC$_{50}$ values of drugs were obtained using peak tail currents during the −40 mV step by nonlinear least-squares fit of the data (GraphPad Software, Inc. San Diego, Calif.).

Example 8—CYP3A4 Inhibition Protocol

Examples 2-3 of the present application and example No. 37 from WO2015/082533 were tested for CYP3A4 inhibition using two different probes: midazolam and testosterone.

The assay procedure is described below and results are presented in Table 2.

Detailed Assay Description

Test compound dissolved in DMSO at selected concentrations was added to a phosphate buffer (50 mM, pH 7.4) containing human liver microsomes (0.1 mg/mL), MgCl (6 mM) and EDTA (0.5 mM) and CYP3A probe substrate, either midazolam (3 µM). Test compound was evaluated at the concentrations 1, 3, 10 and 30 µM and the final DMSO concentration in the incubation was 0.5%. After addition of 1 M NADPH the mixture was incubated at 37° C. for 10 min (midazolam) or 30 min (testosterone). The reaction was terminated by addition of cold CH3CN containing internal standard, centrifuged and formation of the CYP3A specific metabolite (either 1'-hydroxymidazolam or 6-β-hydroxytestosterone) was quantified by UPLC-MS/MS. The relative CYP3A activity at each test concentration was calculated and IC$_{50}$ values determined using XLfit.

TABLE 2

| Example No | CYP3A4 inhibition Assay IC$_{50}$, µM | | hERG inhibition Assay IC$_{50}$, µM |
| --- | --- | --- | --- |
| | Midazolam probe | Testosterone probe | |
| 37 | 10 | 2.8 | 4.3 |
| 2 | 24 | 13 | 14.2 |
| 3 | >30 | 16 | 11.2 |

The present application provides novel RORγ modulator compounds, Examples 2 and 3, which inhibit RORγ activity and for which both hERG inhibition and CYP3A4 inhibition were decreased when compared to prior art compound (example 37 from WO2015/082533). It therefore appears that compounds of (Formula IA) and of (Formula IB) limit the risks of cardiac safety issues and potential adverse toxic effects related to drug-drug interactions respectively while maintaining the RORγ modulation activity.

Example 9, 10, 11, 12 and 13: Synthesis of the Prodrugs

Example 9—Compound of (Formula VI): 2-[4-(cyclopropylmethylsulfinyl)phenyl]-N-[4-[1-(difluoromethyl)-2,2,2-trifluoro-1-hydroxy-ethyl]phenyl]acetamide

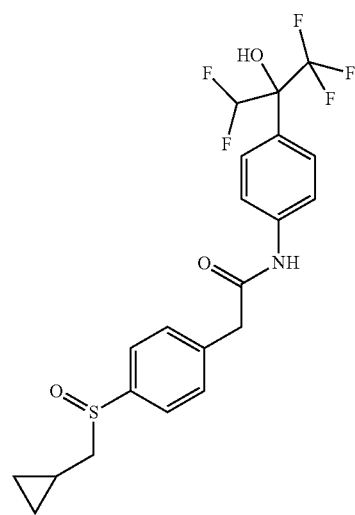

Step 1:

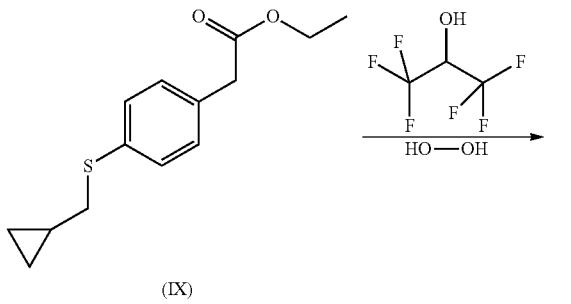

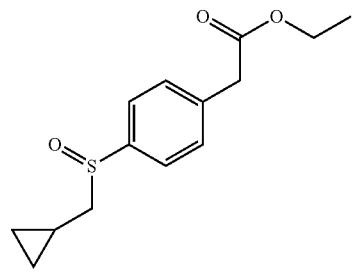

In a 100 mL three-neck round bottom flask placed under argon, hydrogen peroxide (2.64 mL, 25.88 mmol, 30% in water) was added dropwise to a solution of ethyl 2-[4-(cyclopropylmethylsulfanyl)phenyl]acetate (3 g, 11.98 mmol) in 1,1,1,3,3,3-hexafluoropropan-2-ol (12.53 mL, 113.84 mmol). The reaction mixture was stirred for 30 minutes at RT, then a 10% aqueous solution of sodium thiosulfate (50 mL) was added, followed by brine (10 mL). The aqueous layer was extracted twice with EtOAc. The combined organic extracts were washed with brine, dried over Na$_2$SO$_4$, filtered and concentrated under reduced pressure. The residue was taken into ACN (15 mL), concentrated under reduced pressure and dried under high vacuum to obtain 3.16 g of ethyl 2-[4-(cyclopropylmethylsulfinyl)phenyl]acetate as a white solid.

MS(ES$^+$) m/z 267.1 [M+H]$^+$.

$^1$H NMR (400 MHz, DMSO-d6) δ ppm 7.62 (d, J=8.28 Hz, 2 H), 7.46 (d, J=8.28 Hz, 2 H), 4.09 (q, J=7.03 Hz, 2 H), 3.76 (s, 2 H), 2.72-2.87 (m, 2 H), 1.18 (t, J=7.15 Hz, 3 H), 0.82-0.96 (m, 1 H), 0.45-0.61 (m, 2 H), 0.19-0.36 (m, 2 H).

Step 2:

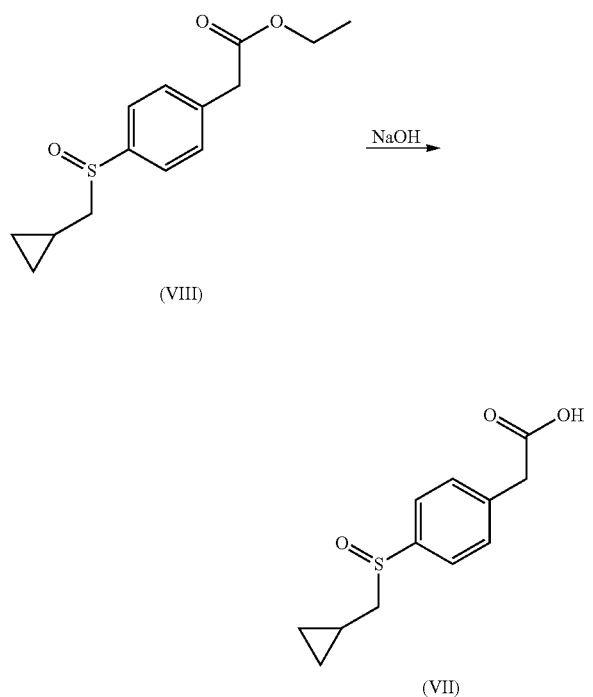

In a 100 mL round bottom flask, a 1M aqueous solution of sodium hydroxide (5.41 mL, 5.41 mmol) was added to a solution of ethyl 2-[4-(cyclopropylmethylsulfinyl)phenyl]acetate (400 mg, 1.50 mmol) in EtOH (25 mL). The reaction mixture was stirred overnight at RT and then concentrated under vacuum. The residue was taken into water, then acidified with an aqueous solution of HCl 1N until reaching pH 1. The aqueous layer was extracted three times with EtOAc. The combined organic layers were washed once with brine, dried over Na$_2$SO$_4$, filtered and concentrated under vacuum to obtain 306 mg of 2-[4-(cyclopropylmethylsulfinyl)phenyl]acetic acid as a white solid.

MS(ES+) m/z 239.1 [M+H]+.

$^1$H NMR (400 MHz, DMSO-d6) δ ppm 7.61 (d, J=8.28 Hz, 2 H), 7.46 (d, J=8.28 Hz, 2 H), 3.66 (s, 2 H), 2.71-2.89 (m, 2 H), 0.85-0.96 (m, 1 H), 0.46-0.64 (m, 2 H), 0.20-0.36 (m, 2 H).

Step 3:

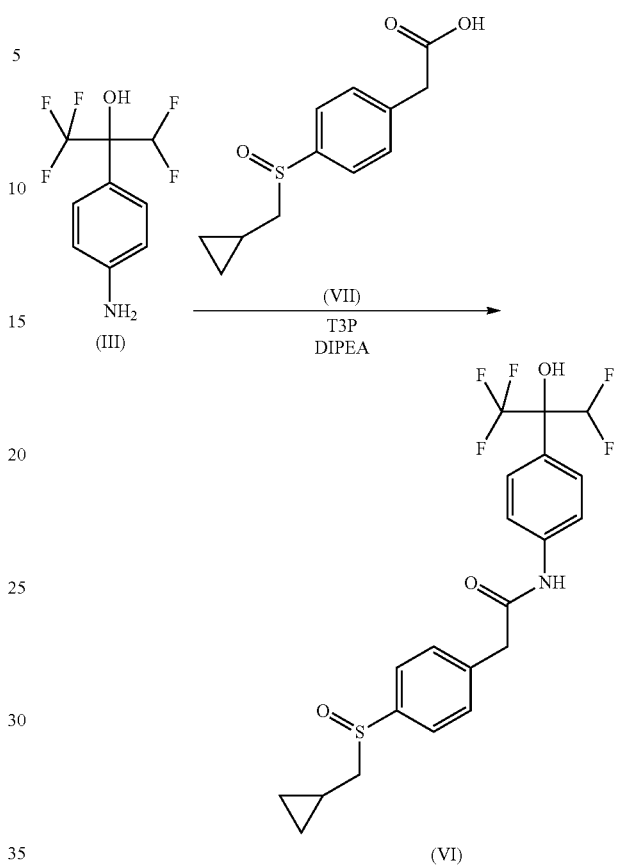

2-(4-aminophenyl)-1,1,1,3,3-pentafluoro-propan-2-ol (151.8 mg, 0.63 mmol), N-ethyl-N-isopropyl-propan-2-amine (0.33 mL, 1.89 mmol) and 2,4,6-Tripropyl-1,3,5,2,4,6-trioxatriphosphinane 2,4,6-trioxide (50% in DCM, 0.48 mL, 0.82 mmol, dropwise) were added to a solution of 2-[4-(cyclopropylmethylsulfinyl)phenyl]acetic acid (150 mg, 0.63 mmol) in DCM (25 mL), which had been prealably placed under argon in an ice bath. After stirring for 30 minutes, the ice bath was removed and the reaction mixture was stirred overnight at RT. Then, DCM and water were added, and the aqueous layer was extracted twice with DCM. The combined organic layers were washed with a saturated aqueous solution of NaHCO$_3$, with a 0.5N aqueous HCl solution, with water, and finally with brine. The organic layer was dried with Na$_2$SO$_4$, filtered and concentrated under vacuum. The residue was purified by column chromatography on silica gel, using from 98% to 95% DCM in MeOH as the eluent to give 206 mg of 2-[4-(cyclopropylmethylsulfinyl)phenyl]-N-[4-[1-(difluoromethyl)-2,2,2-trifluoro-1-hydroxy-ethyl]phenyl]acetamide as an off-white foam.

MS(ES$^+$) m/z 462.0 [M+H]$^+$.

$^1$H NMR (400 MHz, DMSO-d6) δ ppm 10.35 (s, 1 H), 7.45-7.79 (m, 9 H), 6.38-6.88 (m, 1 H), 3.75 (s, 2 H), 2.67-2.90 (m, 2 H), 0.75-0.96 (m, 1 H), 0.45-0.62 (m, 2 H), 0.14-0.37 (m, 2 H).

Examples 10, 11, 12 and 13

The stereoisomers VIA and VID were separated from VI by chiral chromatography using a column Chiralpak AD 20

μm, 350×76.5 mm and a mobile phase, Heptane:EtOH 50:50, 400 mL/min with UV detection at 254 nm.

Starting from 160 mg of racemate in 100 mL of Heptane:EtOH 50:50, one injection of the solution was done to yield, after concentration, 34 mg of Example 10 (first enantiomer to be eluted), 35 mg of Example 13 (last enantiomer to be eluted), and 70 mg of a mixture of Examples 11 and 12.

The stereoisomers VIB and VIC were separated from the corresponding mixture by chiral chromatography using a column Cellulose-4 5 μm, 250×4.6 mm and a mobile phase, Heptane:EtOH 70:30, 45 mL/min with UV detection at 254 nm.

Starting from 70 mg of the mixture in 8 mL of EtOH, four injections of the solution was done to yield, after concentration, 29 mg of VIB (first enantiomer to be eluted), and 30 mg of VIC.

Example 10—Compound of (Formula VIA): (−)-2-[4-[(S)-cyclopropylmethylsulfinyl]phenyl]-N-[4-[(1R)-1-(difluoromethyl)-2,2,2-trifluoro-1-hydroxyethyl]phenyl]acetamide Absolute configuration was assigned arbitrarily.

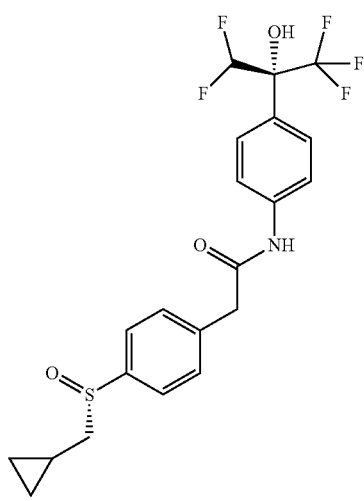

(VIA)

MS(ES+) m/z 462.2 [M+H]+.

$^1$H NMR (400 MHz, DMSO-d6) δ ppm 10.35 (s, 1 H), 7.66 (m, 3 H), 7.63 (d, J=8.4 Hz, 2 H), 7.56 (d, J=9.0 Hz, 2 H), 7.52 (d, J=8.4 Hz, 2 H), 6.64 (t, J=53.2 Hz, 1 H), 3.75 (s, 2 H), 2.82 (dd, J=6.9 et 13.3 Hz, 1 H), 2.74 (dd, J=7.7 et 13.3 Hz, 1 H), 0.89 (m, 1 H), 0.49 a 0.58 (m, 2 H), 0.23 à 0.33 (m, 2 H).

Optical rotation: $[\alpha]_D^{20}$=−63.6° (c=3.8 mg/mL, DMSO).

Example 11—Compound of (Formula VIB): (−)-2-[4-[(S)-cyclopropylmethylsulfinyl]phenyl]-N-[4-[(1S)-1-(difluoromethyl)-2,2,2-trifluoro-1-hydroxyethyl]phenyl]acetamide Absolute configuration was assigned arbitrarily.

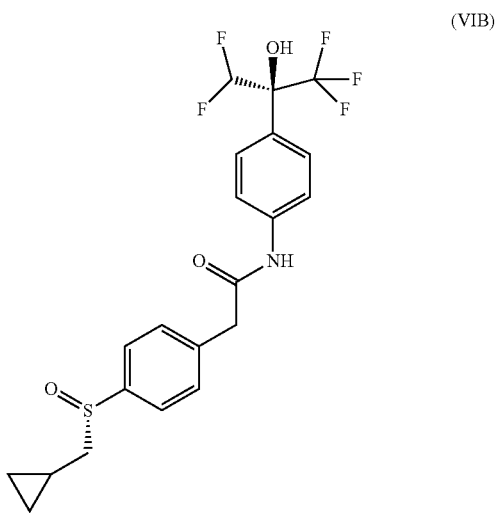 [SMILES: O=C(Cc1ccc([S@@](=O)CC2CC2)cc1)Nc1ccc([C@](O)(C(F)F)C(F)(F)F)cc1]

(VIB)

MS(ES+) m/z 462.2 [M+H]+.

$^1$H NMR (400 MHz, DMSO-d6): δ 10.35 (s, 1 H), 7.66 (m, 3 H), 7.63 (d, J=8.4 Hz, 2 H), 7.56 (d, J=9.0 Hz, 2 H), 7.52 (d, J=8.4 Hz, 2 H), 6.64 (t, J=53.2 Hz, 1 H), 3.75 (s, 2 H), 2.82 (dd, J=6.9 et 13.3 Hz, 1 H), 2.74 (dd, J=7.7 et 13.3 Hz, 1 H), 0.89 (m, 1 H), 0.49 a 0.58 (m, 2 H), 0.23 à 0.33 (m, 2 H).

Optical rotation: $[\alpha]_D^{20}$=−83.1° (c=4.2 mg/mL, DMSO).

Example 12—Compound of (Formula VIC): (+)-2-[4-[(R)-cyclopropylmethylsulfinyl]phenyl]-N-[4-[(1R)-1-(difluoromethyl)-2,2,2-trifluoro-1-hydroxyethyl]phenyl]acetamide Absolute configuration was assigned arbitrarily.

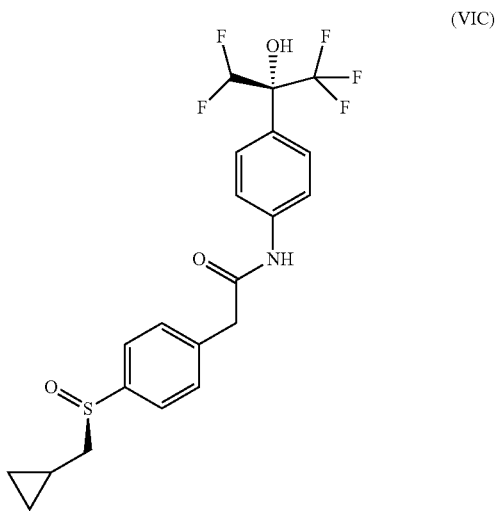 [SMILES: O=C(Cc1ccc([S@](=O)CC2CC2)cc1)Nc1ccc([C@@](O)(C(F)F)C(F)(F)F)cc1]

(VIC)

MS(ES+) m/z 462.0 [M+H]+.

¹H NMR (400 MHz, DMSO-d6): δ 10.35 (s, 1 H), 7.66 (m, 3 H), 7.63 (d, J=8.4 Hz, 2 H), 7.56 (d, J=9.0 Hz, 2 H), 7.52 (d, J=8.4 Hz, 2 H), 6.64 (t, J=53.4 Hz, 1 H), 3.75 (s, 2 H), 2.82 (dd, J=6.9 et 13.3 Hz, 1 H), 2.74 (dd, J=7.7 et 13.3 Hz, 1 H), 0.89 (m, 1 H), 0.49 a 0.58 (m, 2 H), 0.23 a 0.33 (m, 2 H).

Optical rotation: $[\alpha]_D^{20}$=+85.6° (c=5.8 mg/mL, DMSO).

Example 13—Compound of (Formula VID): (+)-2-[4-[(R)-cyclopropylmethylsulfinyl]phenyl]-N-[4-[(1S)-1-(difluoromethyl)-2,2,2-trifluoro-1-hydroxy-ethyl]phenyl]acetamide Absolute configuration was assigned arbitrarily.

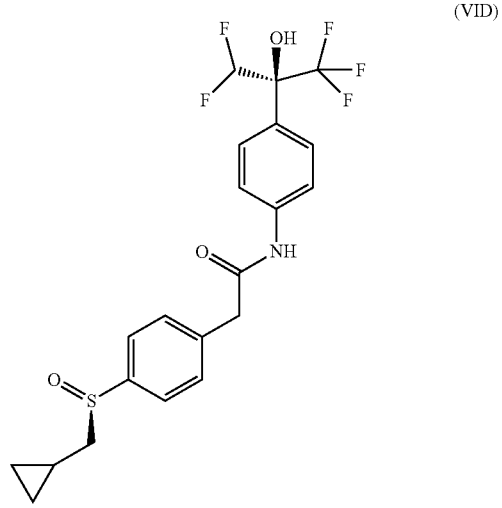 [SMILES: O=C(Cc1ccc([S@](=O)CC2CC2)cc1)Nc1ccc([C@](O)(C(F)F)C(F)(F)F)cc1]

(VID)

MS(ES⁺) m/z 462.0 [M+H]⁺.

¹H NMR (400 MHz, DMSO-d6): δ 10.35 (s, 1 H), 7.66 (m, 3 H), 7.63 (d, J=8.4 Hz, 2 H), 7.56 (d, J=9.0 Hz, 2 H), 7.52 (d, J=8.4 Hz, 2 H), 6.64 (t, J=53.4 Hz, 1 H), 3.75 (s, 2 H), 2.82 (dd, J=6.9 et 13.3 Hz, 1 H), 2.74 (dd, J=7.7 et 13.3 Hz, 1 H), 0.89 (m, 1 H), 0.49 à 0.58 (m, 2 H), 0.23 à 0.33 (m, 2 H).

Optical rotation: $[\alpha]_D^{20}$=+60.9° (c=3.8 mg/mL, DMSO).

Example 14—Aqueous Equilibrated Solubility

Sample Preparation

The studied compound was accurately weighted with a target concentration of 2 mg/mL in an aqueous phosphate buffer (50 mM at pH=7.4). The solution was shaken overnight (rock'n roll shaker) at RT and protected from light (about 24 hrs). The solution was filtered in plate filter device (microplate Millipore "Solvinert" with integrated PTFE filter; 0.45 µm) and the filtrate was dosed by LC/UV method.

Reference (Standard) Preparation

The studied compound was accurately weighted with a target concentration of 0.1 mg/mL in DMSO. The solution was sonicated at RT and protected from light. The reference solution was dosed by a LC/UV method and pH of the solubilized fraction was measured.

TABLE 3

| Example No | Solubility pH 7.5* (µg/mL) |
|---|---|
| 2 | <1.0 |
| 3 | <1.0 |

TABLE 3-continued

| Example No | Solubility pH 7.5* (µg/mL) |
|---|---|
| 9 | 99.4 |
| 10 | 94.8 |
| 11 | 92.5 |
| 12 | 94.4 |
| 13 | 93.0 |

*pH of the solubilized fraction.

The invention claimed is:

1. A pharmaceutical composition in unit dosage form for oral or parenteral administration, said pharmaceutical composition comprising:
    a compound having the absolute configuration corresponding to Formula IA 2-{4-[(cyclopropylmethyl)sulfonyl]phenyl}-N-{4-[(1R)-1-(difluoromethyl)-2,2,2-trifluoro-1-hydroxyethyl]phenyl}acetamide:

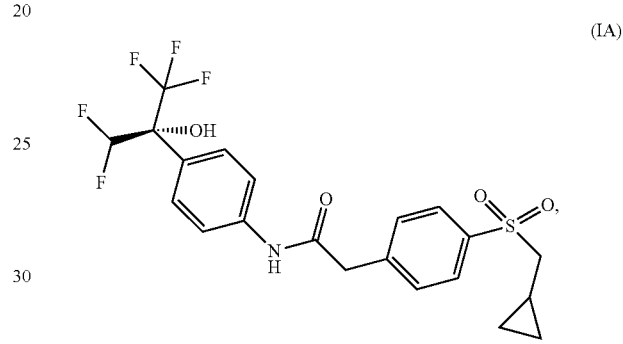

(IA)

or a pharmaceutically acceptable salt thereof; and,
one or more pharmaceutically acceptable excipients.

2. A process of preparing a compound of Formula (IA) comprising:
    i) obtaining 2-(4-bromophenyl)-1,1,1,3,3-pentafluoropropan-2-ol (IV) from 1-(4-bromophenyl)-2,2-fluoroethanone (V) by trifluoromethylation using trifluoromethyltrimethylsilane (TMSCF₃) in the presence of tetra-N-butylammonium fluoride (TBAF):

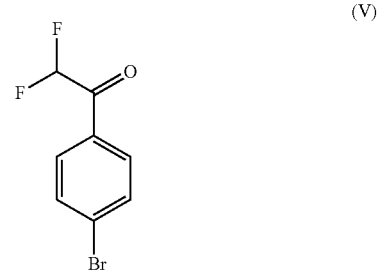

(V)

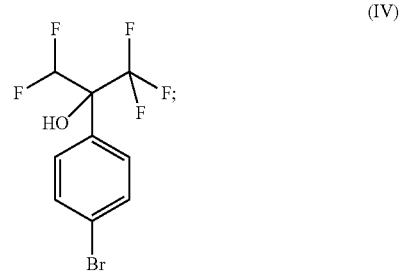

(IV)

ii) obtaining a compound of Formula (II) by amine substitution of the bromine atom of 2-(4-bromophenyl)-1,1,1,3,3-pentafluoro-propan-2-ol (IV):

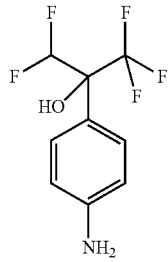

(II)

wherein said substitution is performed using lithium bis(trimethylsilyl)amide), 2-(dicyclohexylphosphino)biphenyl and tris(dibenzylidene acetone)dipalladium;

iii) reacting said amine of formula (II) with a compound of Formula (III):

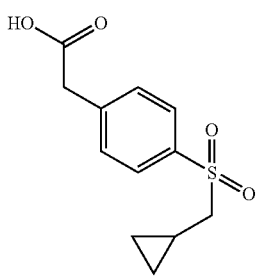

(III)

to give the compound of Formula (I);

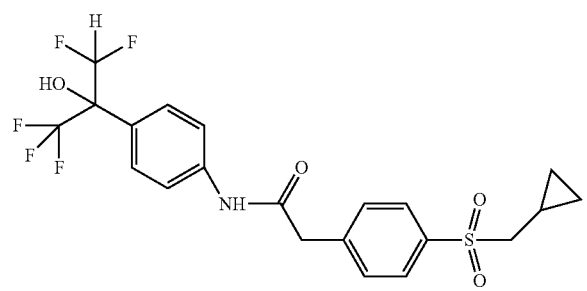

(I)

wherein said reaction is performed in the presence of 1-propanephosphonic anhydride and N,N-diisopropylethylamine; and, iv) obtaining the compound of Formula (IA) by chiral separation

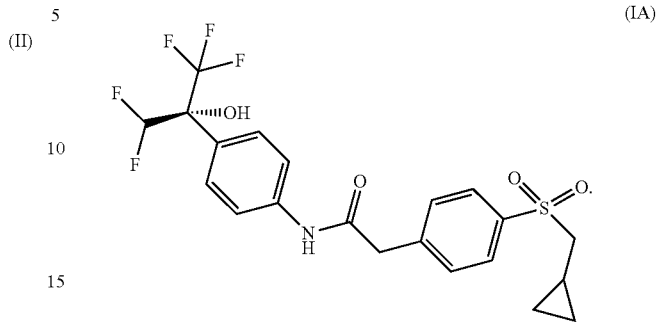

(IA)

3. A method for treatment of at least one condition selected from the group consisting of multiple sclerosis, inflammatory bowel disease, Crohn's disease, psoriasis, rheumatoid arthritis, asthma, osteoarthritis, Kawasaki disease, Hashimoto's thyroiditis and mucosal leishmaniasis, said method comprising administering to a person in need of the treatment a pharmaceutical composition comprising one or more pharmaceutically acceptable excipients and from 0.0001-100 mg per kilogram of bodyweight of a compound having the absolute configuration corresponding to Formula IA or a pharmaceutically acceptable salt thereof, wherein Formula IA is 2-{4-[(cyclopropylmethyl)sulfonyl]phenyl}-N-{4-[(1R)-1-(difluoromethyl)-2,2,2-trifluoro-1-hydroxyethyl]phenyl}acetamide:

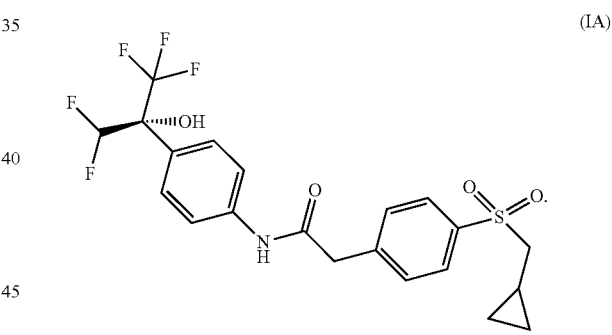

(IA)

4. The method according to claim 3, wherein the at least one condition is selected from the group consisting of rheumatoid arthritis, psoriasis, inflammatory bowel disease, Crohn's disease and multiple sclerosis.

5. The method according to claim 3, wherein the at least one condition is selected from osteoarthritis and asthma.

6. The method according to claim 3, wherein the at least one condition is mucosal leishmaniasis.

* * * * *